(12) United States Patent
Huang et al.

(10) Patent No.: US 10,026,901 B2
(45) Date of Patent: Jul. 17, 2018

(54) ORGANIC ELECTRONIC MATERIAL AND ORGANIC ELECTROLUMINESCENT DEVICE

(71) Applicants: GUANGDONG AGLAIA OPTOELECTRONIC MATERIALS CO., LTD, Foshan, Guangdong (CN); BEIJING AGLAIA TECHNOLOGY DEVELOPMENT CO., LTD, Beijing (CN)

(72) Inventors: Jinhai Huang, Beijing (CN); Lei Dai, Beijing (CN); Jinxin Chen, Foshan (CN); Lifei Cai, Beijing (CN)

(73) Assignees: GUANGDONG AGLAIA OPTOELECTRONICS MATERIALS CO., LTD, Foshan (CN); BEIJING AGLAIA TECHNOLOGY DEVELOPMENT CO., LTD, Beijing (CN)

( * ) Notice: Subject to any disclaimer, the term of this patent is extended or adjusted under 35 U.S.C. 154(b) by 547 days.

(21) Appl. No.: 14/404,609

(22) PCT Filed: Jun. 5, 2013

(86) PCT No.: PCT/CN2013/076758
§ 371 (c)(1),
(2) Date: Nov. 30, 2014

(87) PCT Pub. No.: WO2013/182046
PCT Pub. Date: Dec. 12, 2013

(65) Prior Publication Data
US 2015/0108449 A1    Apr. 23, 2015

(30) Foreign Application Priority Data
Jun. 6, 2012    (CN) .......................... 2012 1 0185154

(51) Int. Cl.
*H01L 51/54*    (2006.01)
*C09K 11/06*    (2006.01)
(Continued)

(52) U.S. Cl.
CPC .......... *H01L 51/0054* (2013.01); *C07C 13/66* (2013.01); *C07C 13/72* (2013.01);
(Continued)

(58) Field of Classification Search
CPC .. C07F 7/08; C07F 7/0809; C07F 9/53; C07F 9/5325; C07F 9/5329; C07F 15/00;
(Continued)

(56) References Cited

U.S. PATENT DOCUMENTS

2006/0170336 A1* 8/2006 Ono ...................... H01L 27/322
                                                              313/504
2008/0071122 A1    3/2008 Inoue et al.
(Continued)

FOREIGN PATENT DOCUMENTS

CN    101730947 A    6/2010
KR    2011-0137897 A    12/2011
(Continued)

OTHER PUBLICATIONS

Machine translation of KR20110137897. Date of publication: Dec. 2011.*

(Continued)

*Primary Examiner* — Andrew K Bohaty
(74) *Attorney, Agent, or Firm* — Maschoff Brennan

(57) ABSTRACT

An organic light-emitting material having the structure of formula (I) or (II) as described below and an organic light-emitting device (OLED) are disclosed. The OLED adopts the compound containing fluoranthene group as the electron transport material possessing good electron transport and injection ability. The material also enhances the luminous efficiency and lifetime of the device because of its excellent thermal stability and film-forming properties. At the same time, the high triplet energy and excellent electron transport capacity of the material containing fluoranthene group make it suitable to be used as the host for phosphorescent devices, increasing the number of electrons in the light-emitting layer and the efficiency of the device.

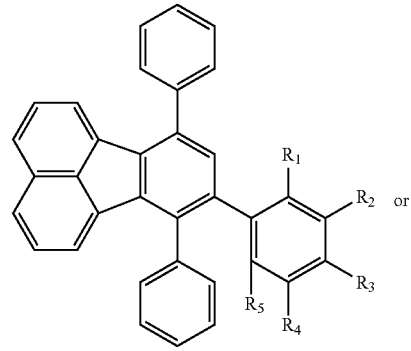

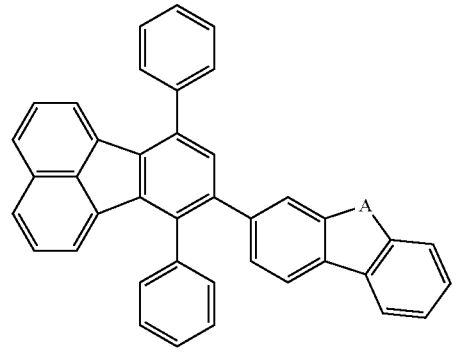

19 Claims, 4 Drawing Sheets

(51) Int. Cl.
| | |
|---|---|
| H01L 51/00 | (2006.01) |
| C07F 9/53 | (2006.01) |
| C07D 333/76 | (2006.01) |
| C07F 15/00 | (2006.01) |
| C07D 235/18 | (2006.01) |
| C07C 211/54 | (2006.01) |
| C07D 239/26 | (2006.01) |
| C07D 249/08 | (2006.01) |
| C07D 251/24 | (2006.01) |
| C07D 271/107 | (2006.01) |
| C07D 209/86 | (2006.01) |
| C07C 13/66 | (2006.01) |
| C07D 213/06 | (2006.01) |
| C07D 213/16 | (2006.01) |
| C07D 307/91 | (2006.01) |
| C07F 7/08 | (2006.01) |
| C07D 235/20 | (2006.01) |
| C07C 13/72 | (2006.01) |
| C09B 57/00 | (2006.01) |
| C09B 69/00 | (2006.01) |
| C07D 235/08 | (2006.01) |
| H01L 51/50 | (2006.01) |

(52) U.S. Cl.
CPC .......... *C07C 211/54* (2013.01); *C07D 209/86* (2013.01); *C07D 213/06* (2013.01); *C07D 213/16* (2013.01); *C07D 235/08* (2013.01); *C07D 235/18* (2013.01); *C07D 235/20* (2013.01); *C07D 239/26* (2013.01); *C07D 249/08* (2013.01); *C07D 251/24* (2013.01); *C07D 271/107* (2013.01); *C07D 307/91* (2013.01); *C07D 333/76* (2013.01); *C07F 7/0809* (2013.01); *C07F 9/5325* (2013.01); *C07F 9/5329* (2013.01); *C07F 15/0033* (2013.01); *C09B 57/00* (2013.01); *C09B 57/008* (2013.01); *C09B 69/008* (2013.01); *C09K 11/06* (2013.01); *H01L 51/0058* (2013.01); *H01L 51/0067* (2013.01); *H01L 51/0072* (2013.01); C07C 2603/18 (2017.05); C07C 2603/40 (2017.05); C07C 2603/94 (2017.05); C09K 2211/1007 (2013.01); C09K 2211/1011 (2013.01); C09K 2211/1014 (2013.01); C09K 2211/1029 (2013.01); C09K 2211/1044 (2013.01); C09K 2211/1048 (2013.01); C09K 2211/1051 (2013.01); C09K 2211/1059 (2013.01); *H01L 51/0094* (2013.01); *H01L 51/5016* (2013.01); *H01L 51/5072* (2013.01)

(58) Field of Classification Search
CPC .. C07F 15/0033; C07F 15/0086; C07C 13/00; C07C 13/28; C07C 13/32; C07C 13/54; C07C 13/66; C07C 13/72; C07C 211/43; C07C 211/54; C07C 2103/18; C07C 2103/40; C07C 2103/94; C07D 209/86; C07D 211/54; C07D 213/00; C07D 213/06; C07D 213/16; C07D 235/00; C07D 235/08; C07D 235/18; C07D 235/20; C07D 239/00; C07D 239/26; C07D 249/00; C07D 249/08; C07D 251/00; C07D 251/24; C07D 271/00; C07D 271/107; C07D 333/00; C07D 333/76; C07D 307/00; C07D 307/91; C09K 11/06; H01L 51/0032; H01L 51/005; H01L 51/0051; H01L 51/0052; H01L 51/0053; H01L 51/0054; H01L 51/0055; H01L 51/0057; H01L 51/0058; H01L 51/0059; H01L 51/006; H01L 51/0062; H01L 51/0067; H01L 51/0061; H01L 51/0069; H01L 51/007; H01L 51/0072; H01L 51/0073; H01L 51/0074; H01L 51/0094; H01L 51/50; H01L 51/5012; H01L 51/5016; H01L 51/5056; H01L 51/5072; H01L 51/5092; C09B 57/00; C09B 57/008; C09B 69/00
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

| 2009/0108735 A1* | 4/2009 | Begley .................... C07C 13/62 313/504 |
| 2009/0108736 A1* | 4/2009 | Begley ................ H01L 51/0052 313/504 |

FOREIGN PATENT DOCUMENTS

| KR | 20110137897 A | * 12/2011 |
| WO | 2009/008348 A1 | 1/2009 |
| WO | 2009/008352 A1 | 1/2009 |

OTHER PUBLICATIONS

Baldo M. A., High-Efficiency Fluorescent Organic Light-Emitting Devices Using a Phosphorescent Sensitizer, Forrest S. R. Et al, Nature, 1998, 395, 151-154.
Bhattacharya, S. et al., Electronic Structures and Ionicity in [60]fullerene/polycyclic aromatic hydrocarbon charge by UV-Vis and NMR. Journal of Molecular Structure. 2006, vol. 784, Nos. 1-3, pp. 124-137.
Kim et al., "Substituent Effect of Fluoranthene Derivatives in Electroluminescence." Molecular Crystals and Liquid Crystals 498.1 (2009): 140-150.
Tang et al., Organic Electroluminescent Diodes, Applied Physics Letter 1987, 51, pp. 913-916.
Tong, Qingxiao et al., A high performance nondoped blue organic 1 Light-emitting device based on a diphenylfluoranthene-sSubstituted florene derivative. Journal of Physical Chemistry C. 2009, vol. 113, No. 15, pp. 6227-6230.
Tong, Qing-Xiao, et al. Efficient green organic light-Emitting devices with a nondoped dual-functional electroluminescent material. Applied Physics Letters 91.15 (2007): 153504-153504.
Tong, Qing-Xiao, et al. High-efficiency undoped blue organic light-emitting device. Dyes and Pigments 86.3 (2010): 233-237.

\* cited by examiner

ORGANIC ELECTRONIC MATERIAL AND ORGANIC ELECTROLUMINESCENT DEVICE

TECHNICAL FIELD

This invention relates to a new type of organic electronic material. By vacuum deposition into thin film, it is used in organic light emitting diodes as an electron transport material and phosphorescence host material. This invention belongs to the organic light-emitting device (OLED) display technical field.

BACKGROUND ART

OLED, as a new type of display technology, has unique advantages such as self-illumination, wide viewing angle, low power consumption, high efficiency, thin, rich colors, fast response, extensive application temperature range, low driving voltage, applicable for flexible and transparent display panel, and environmental friendliness, etc. Therefore, OLED technology can be applied to flat panel displays and new generation of lighting, or can be used as backlight of LCD. In 1987, Kodak (Tang et al) firstly made a sandwiched bilayer devices using 8-hydroxyquinoline aluminum (Alq3) as the light emitting layer and a triphenylamine derivative as the hole transporting layer through thin-film vacuum evaporation technique. The device achieved a luminance up to 1000 cd/m$^2$ at a driving voltage of 10 V (Tang C. W., Vanslyke S. A. Appl. Phys. Lett. 1987, 51, 913-916). This technological breakthrough had aroused widespread notice in the scientific community and industry, and since then the research and applications of organic light-emitting technology become a hot issue. Subsequently, in 1989, with the invention of host-guest emission technology, the luminous efficiency and lifetime of OLED had been greatly improved. In 1998, Forrest et al found the electrophosphorescence, which lifted the theoretical limit of organic electroluminescent quantum efficiency from 25% to 100% (Baldo M. A., Forrest S. R. Et al, Nature, 1998, 395, 151-154), bringing the research of organic light-emitting technology into a new era with extended field of research.

A classic three-layer OLED comprises a hole transport layer, a light emitting layer and an electron transport layer. adopts traditional electron transport material is Alq$_3$, which has good film-forming propertiy and thermal stability, but its strong green emission and low electron mobility restricts its industrial applications. Subsequently, some electron transport materials with excellent performance, such as TPBI, BCP, Bphen, are also widely used in the OLED. The existing material of light-emitting layer can be divided into two categories, namely, fluorescent material and phosphorescent material, which are often adopted in guest-host doping technology.

CBP (4,4'-bis(9-carbazolyl)-biphenyl) is a highly efficient and high-triplet-energy phosphorescent host material. When CBP is used as the host material, triplet energy can be smoothly transferred to phosphorescent material, producing efficient red and green emission. However, such representative host materials are restricted to use because of their poor thermal stability and short lifetime of manufactured devices.

Although OLED has made considerable progress after 20 years of development, and organic materials have also been in constant development, there are still very few materials that can meet the market demands with good device efficiency and lifetime to give excellent performance and stability at the same time.

Fluoranthene, as an electroluminescent material, is widely used as electron transport material, hole transport material and light-emitting material. However, according to the known reports, either the performances of devices are not described in details, or the devices only had low efficiency or poor stability. In the present invention, a series of new compounds based on fluoranthene are disclosed and used in OLEDs.

SUMMARY OF THE INVENTION

The purpose of the present invention is to provide the synthesis method of a novel organic compound which is used in electroluminescent devices as an electron-transport and/or a phosphorescent host material, and the preparation method of high performance OLEDs using the invented material hereof.

The organic electronic material in the present invention has a chemical structural formula (I) or (II).

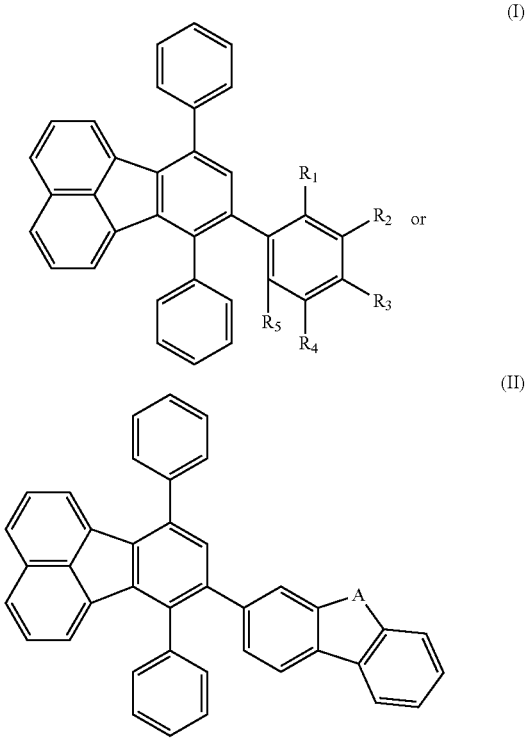

wherein, any four of $R_1$-$R_5$ are hydrogen, and the other is C1-C6 alkyl, C7-C24 aryl, substituted or unsubstituted heteroaromatic ring(s) having one or more heteroatoms (N, O, S), triaryl silyl, diarylamino, diaryl phosphine oxide, aromatic carbonyl, arylthio; or $R_1$, $R_1$, $R_3$, $R_5$ are hydrogen, $R_2$, $R_4$ independently represent C1-C6 alkyl, C6-C24 aryl, heteroaromatic ring(s) with one or more heteroatoms (N, O, S), triaryl silyl, diarylamino, diaryl phosphine oxide, aromatic carbonyl, arylthio, A represents $C(R_6)_2$, $N(R_7)$, S, O, $P(R_8)$, $S(O)_2$ or $B(R_9)$, $R_6$-$R_9$ independently represent hydrogen, deuterium, alkyl, phenyl, alkylphenyl, heteroaromatic ring with one or more heteroatoms (N, O, S), a cyclized structure formed between two R6 and C.

Preferably, $R_1$-$R_5$ are five-membered or six-membered heteroaromatic ring substituted with fluorenyl or alkyl or phenyl or naphthyl, diphenyl amino, phenyl-naphthylamine, triphenylsilyl, diphenyl phosphine oxide, phenyl carbonyl or phenyl sulfonyl.

Wherein, the said five-membered or six-membered heteroaromatic ring is carbazolyl, pyrimidinyl, pyridyl, thiazolyl, triazole group or triazine group.

The said fluorenyl is 9,9-dimethyl-fluorenyl, 9,9-diphenyl fluorenyl, 9,9-di-p-tolyl-9H-fluorenyl or spiro fluorenyl.

In one aspect, the said $R_1$, $R_2$, $R_4$, $R_5$ are hydrogens.

Preferably, A is $C(R_6)_2$, $N(R_7)$, S, O, $S(O)_2$; $R_6$-$R_7$ are hydrogen, methyl, phenyl, methyl phenyl, or five-membered cyclic structure formed between two $R_6$ and C.

Preferably the compounds in the present invention are exemplified as but not limited to the follows:

1

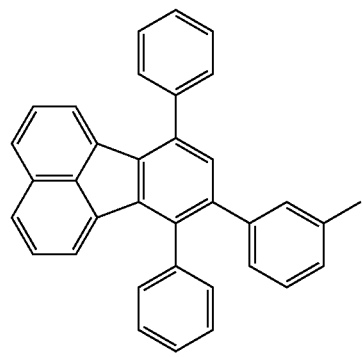

2

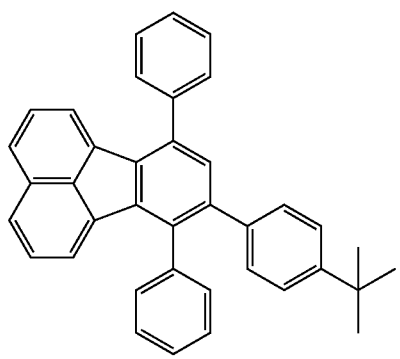

3

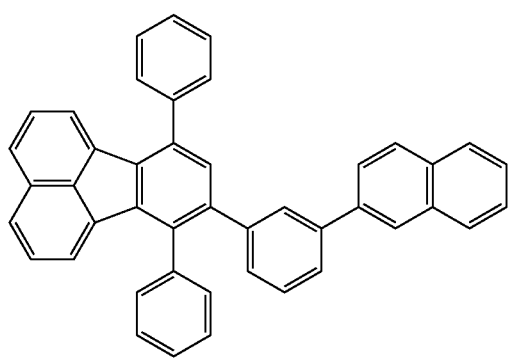

4

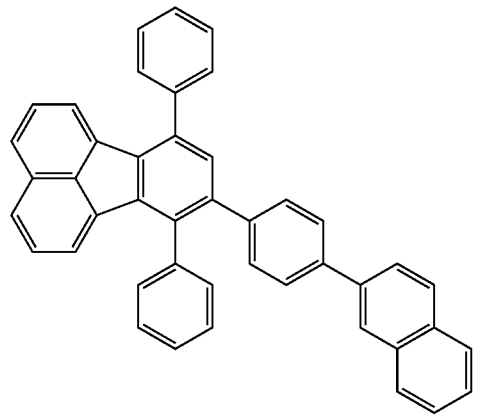

5

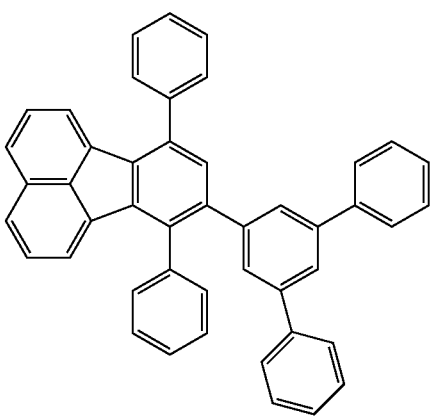

6

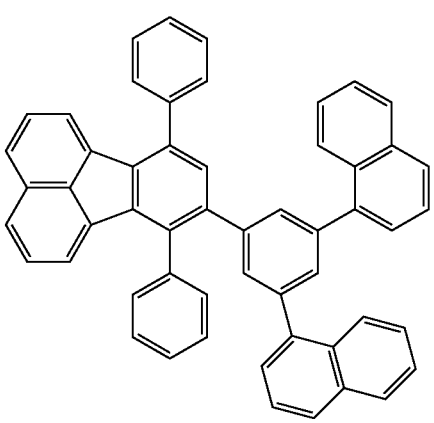

7

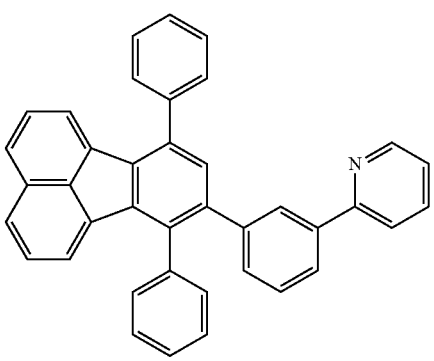

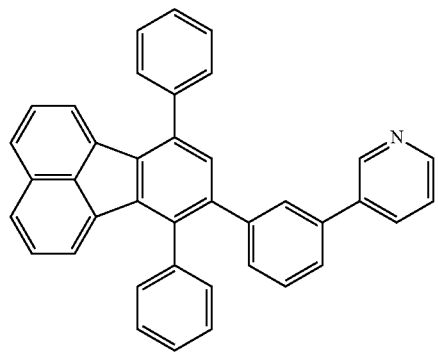
8
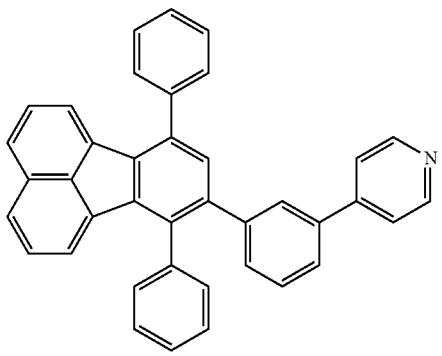
9
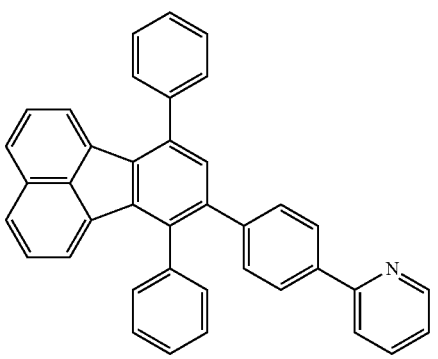
10
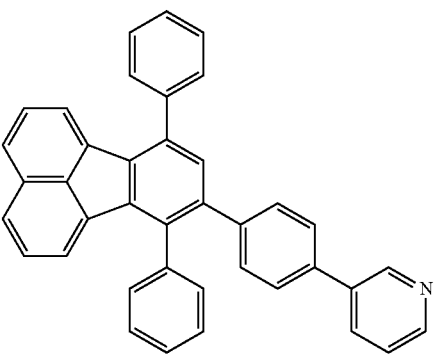
11

16
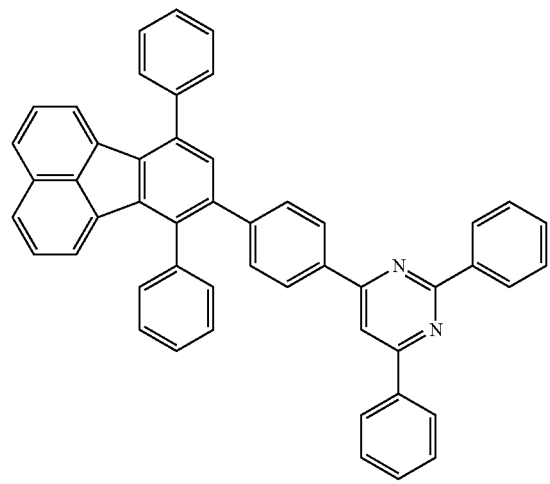
17
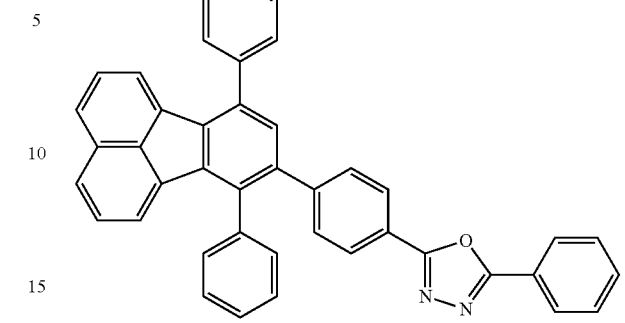
18
19
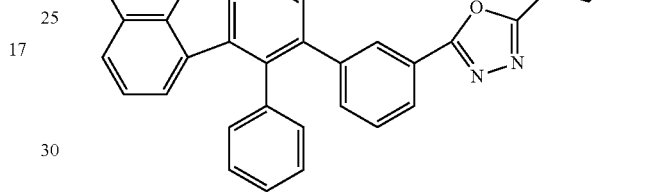
20
21
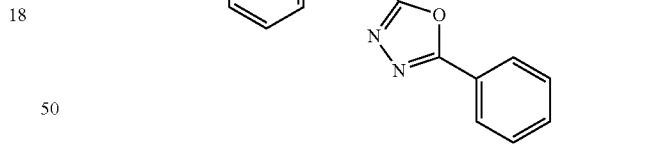
22
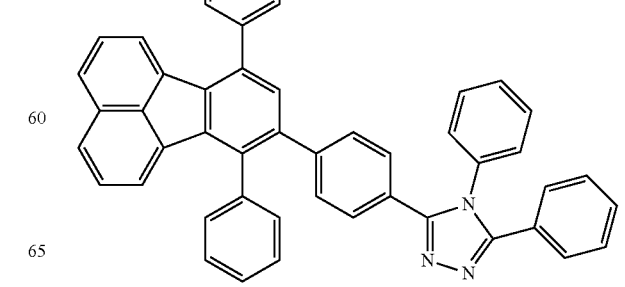

23
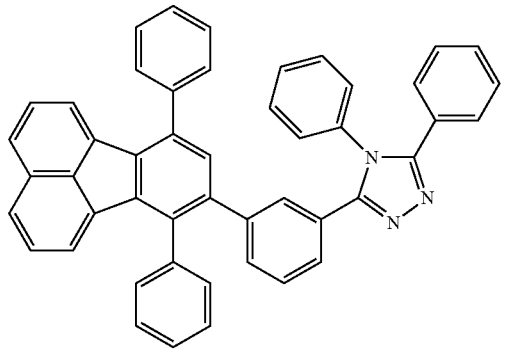
24
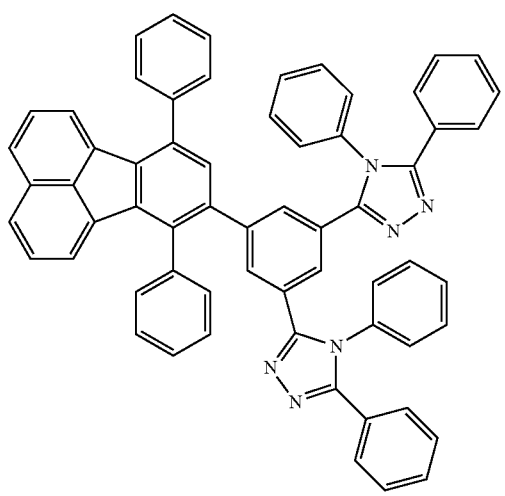
25
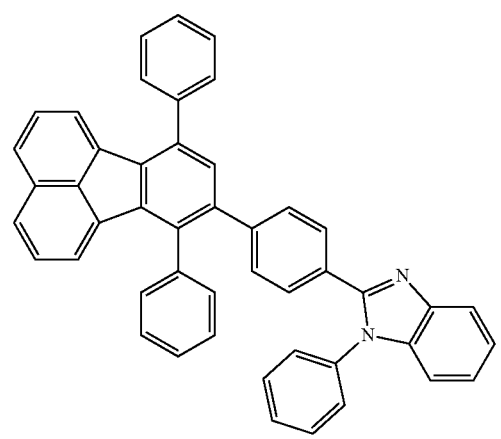
26
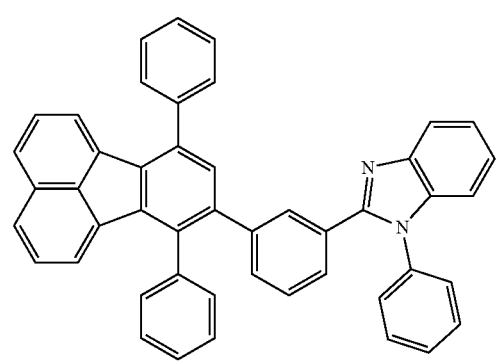
27
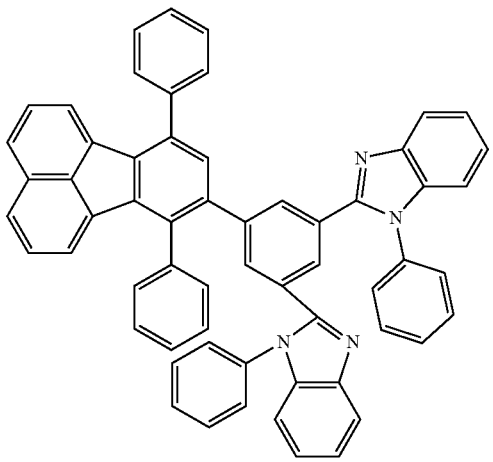
28
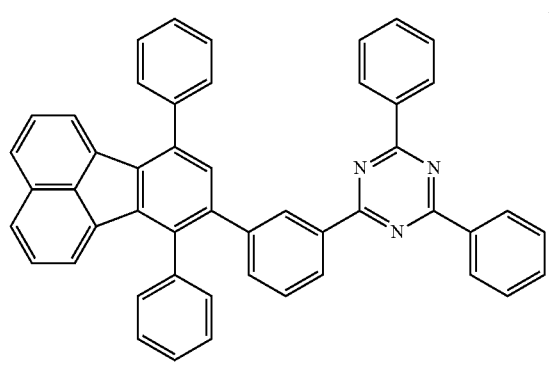
29

30
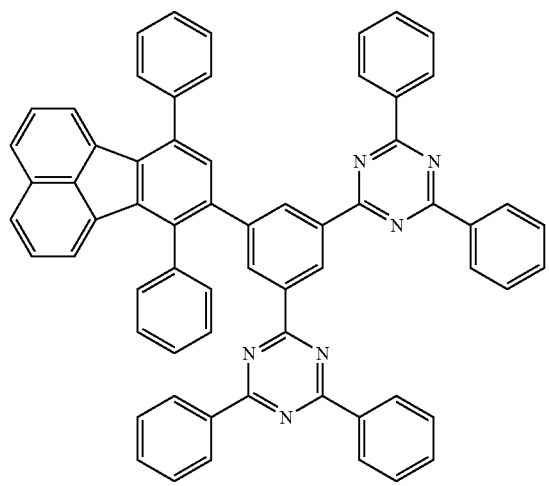
31
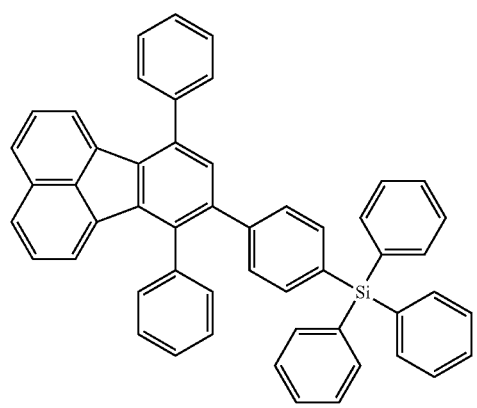
32
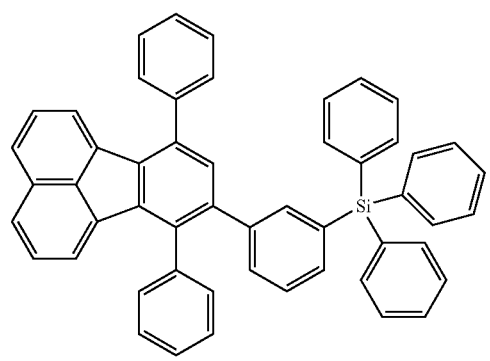
33
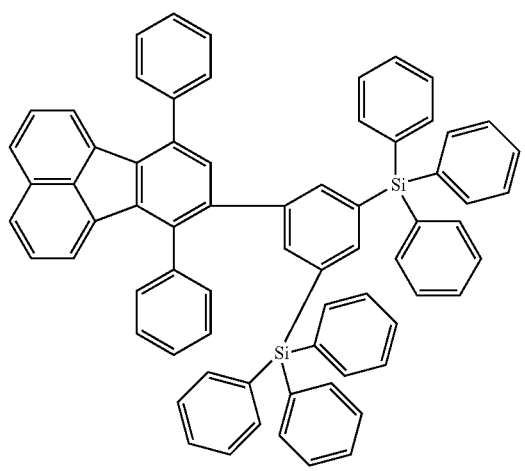
34
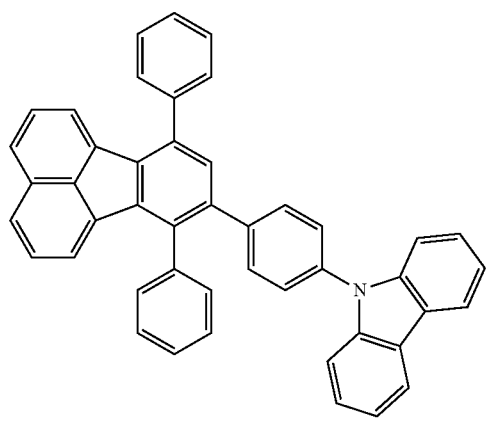
35

36
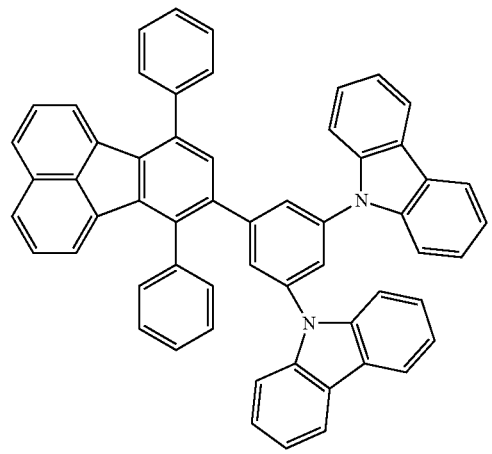
37
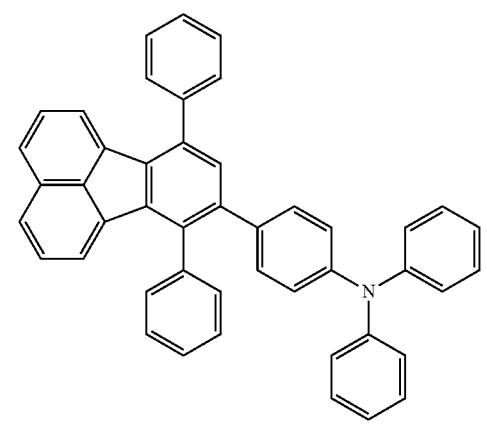
38
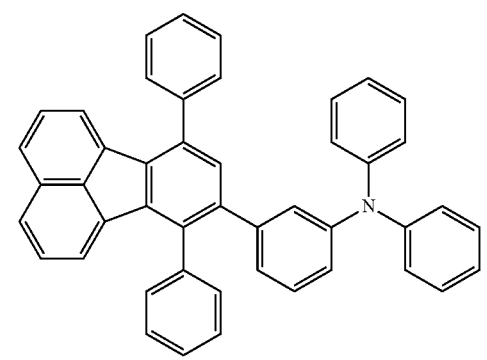
39
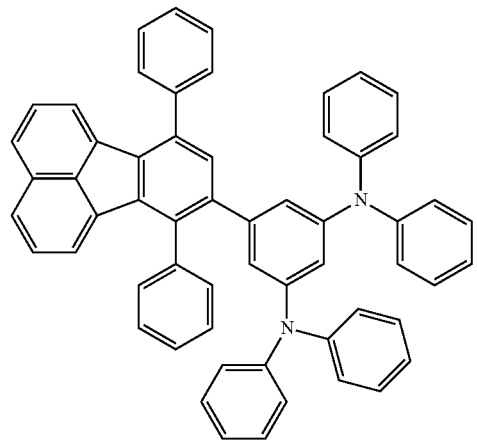
40
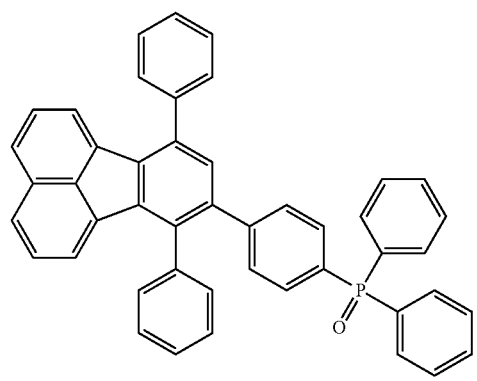
41
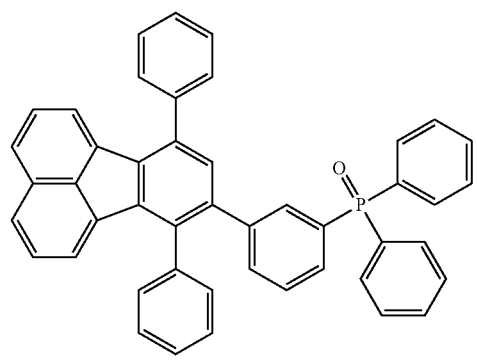
42
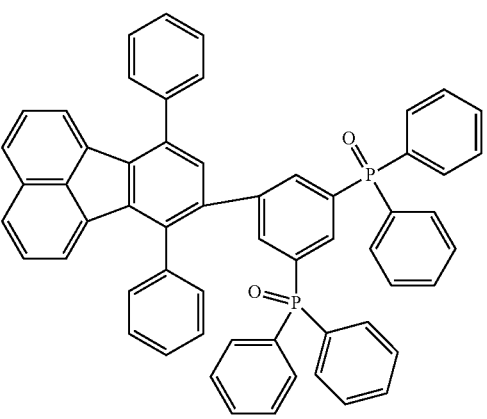

43
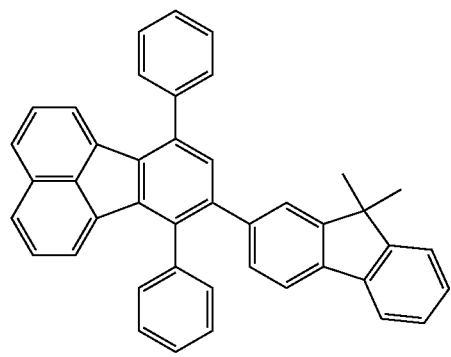
44
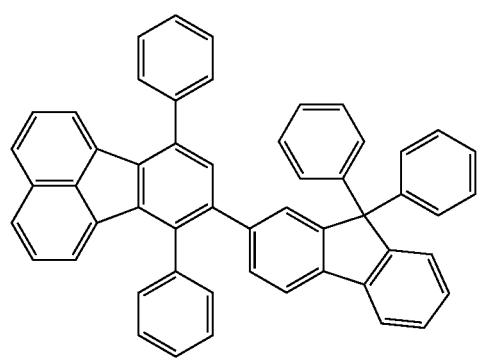
45
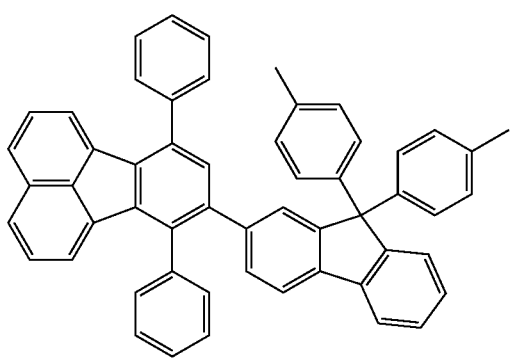
46
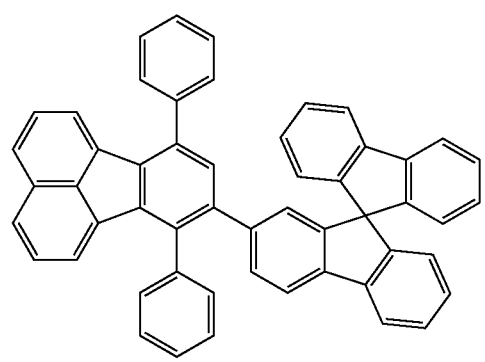
47
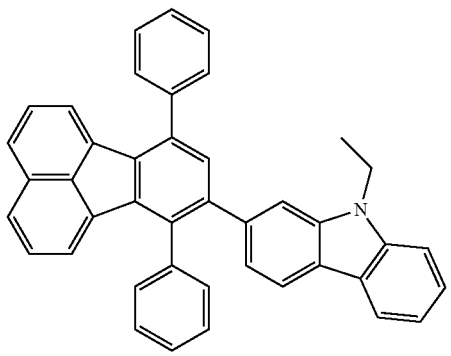
48
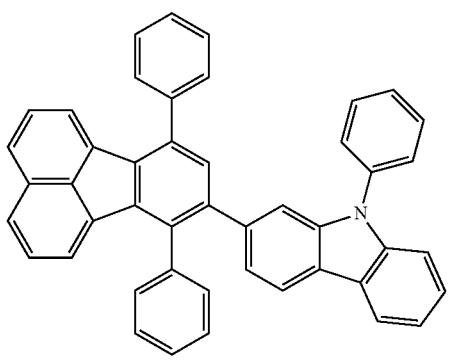
49
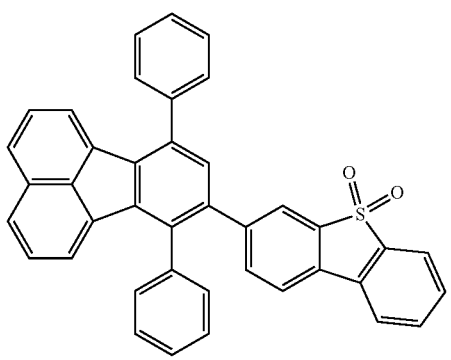
50
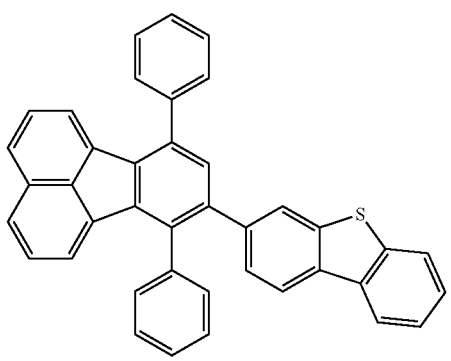

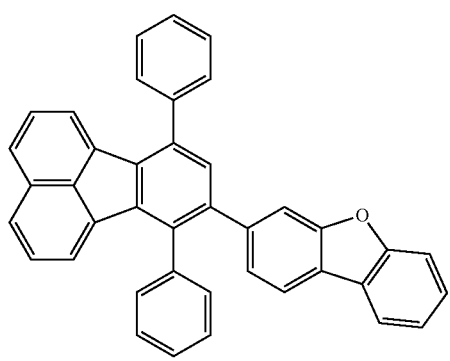

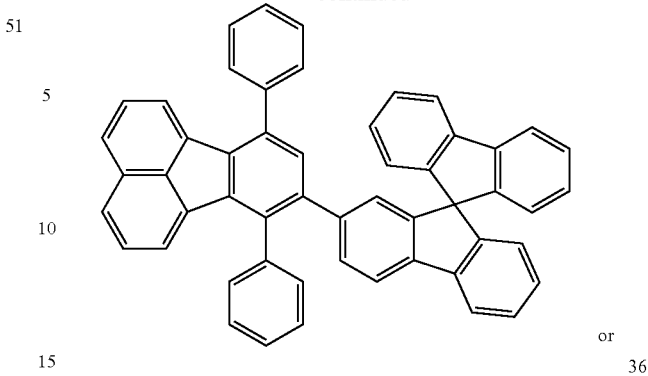

or

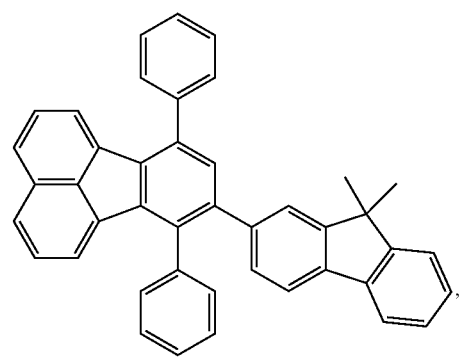

More preferably:

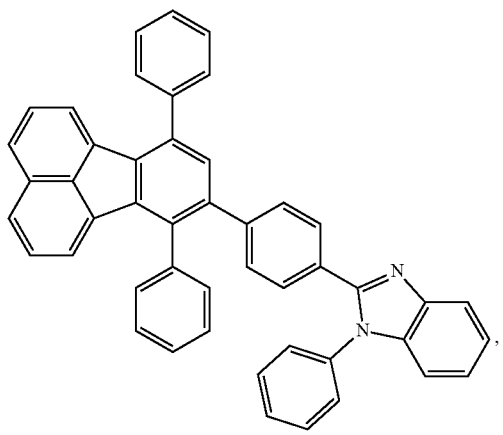

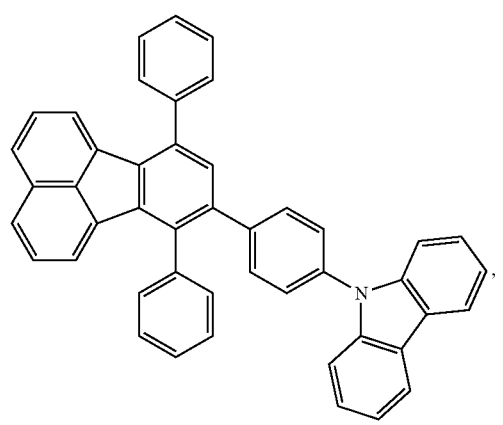

The OLED of the present invention comprises a substrate, an anode layer formed on the substrate, a hole injection layer, a hole transport layer, a light emitting layer, an electron transport layer and an electron injection layer evaporated sequentially above the anode layer, as well as a cathode.

The light-emitting layer may be a fluorescent light-emitting layer or a phosphorescent light-emitting layer.

In one embodiment of OLED in the present invention, the invented compounds are used as an electron transporting material;

In another embodiment of OLED in the present invention, the invented compounds are used as phosphorescent host material, and the guest material is preferably an organic iridium compound or an organic platinum compound;

In another embodiment, the OLED in the present invention adopts the above compounds as a phosphorescent host as well as an electron transport layer.

The OLED adopts the compound containing fluoranthene group as the electron transport material, which has good electron transport and injection ability. The material also enhances the luminous efficiency and lifetime of the device because of its excellent thermal stability and film-forming properties. At the same time, the high triplet energy and excellent electron transport capacity of the material containing fluoranthene group make it suitable to be used as the host for phosphorescent devices, increasing the number of electrons in the light-emitting layer and the efficiency of the device.

DETAILED DESCRIPTIONS OF EMBODIMENTS

Figure 1:
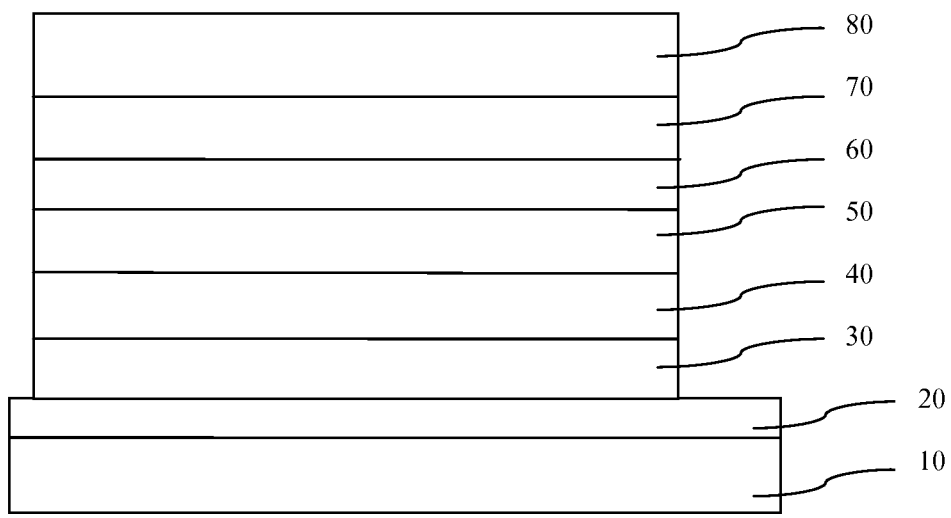
FIG. 1 is a structural drawing of the device, of which, 10 denotes a glass substrate, 20 denotes an anode, 30 denotes a hole injection layer, 40 denotes a hole transport layer, 50 denotes a light emitting layer, 60 denotes an electron transport layer, 70 denotes an electron injection layer, 80 denotes a cathode.

In the following, the present invention is described in details by the following embodiments.

Embodiment 1: Synthesis of Compound 43

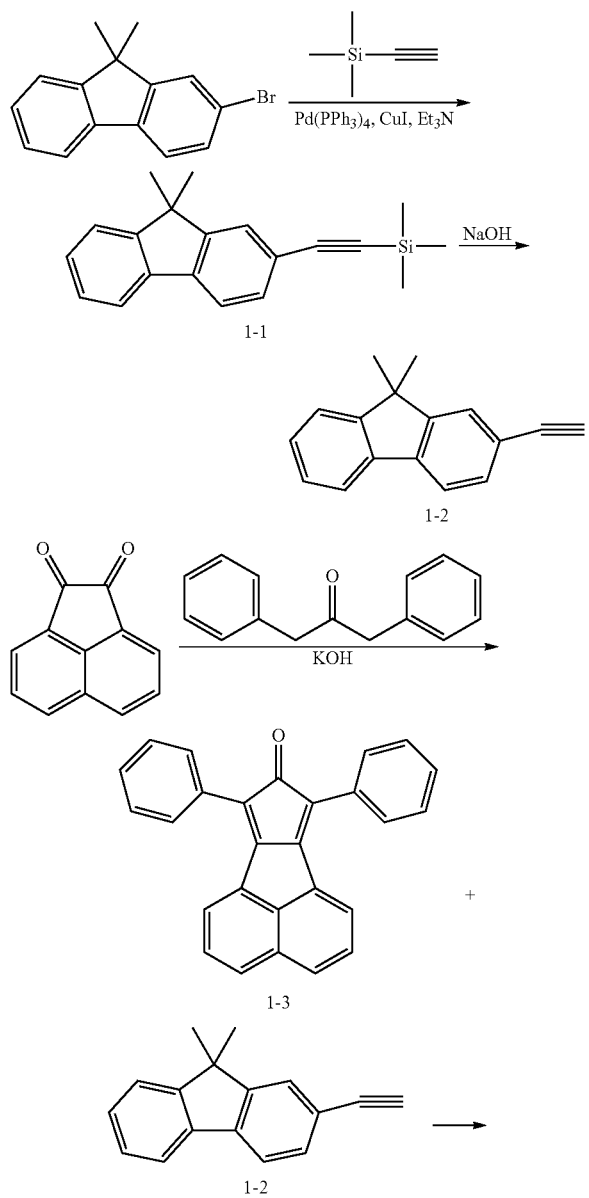

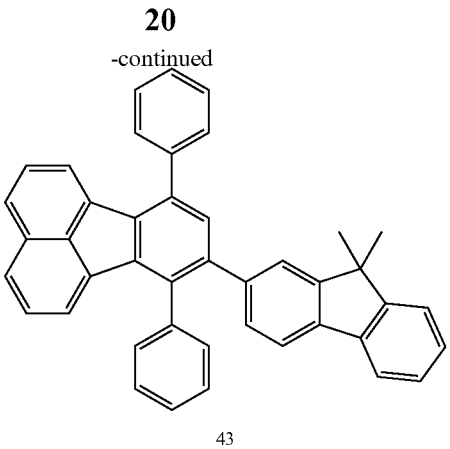

43

Synthesis of Intermediate 1-1

Triethylamine was added to a mixture of 7.5 g 2-bromo-9,9-dimethyl-fluorine, 0.15 g cuprous iodide, and 0.3 g tetrakis(triphenylphosphine)palladium, under nitrogen. The starting materials were stirred until fully dissolved, and then 10 ml trimethylsilyl acetylene was added followed by refluxing for 12 hours overnight. The solvent was removed under reduced pressure, the residue was extracted three times using diethyl ether/water. The organic phase was washed three times with saturated brine, dried over sodium sulfate, filtered, and concentrated to get 6.8 g product, with a yield of 85%.

Synthesis of Intermediate 1-2

45 ml methanol, 50 ml methylene chloride, 5 g potassium hydroxide, 6.8 g intermediate 1-1 were added to a flask under nitrogen and stirred for 1 hour. The mixture is filtered to remove the inorganic salts, and the organic solvent was removed under reduced pressure. The precipitate was recrystallized from methanol to get 4.2 g product, with a yield of 82%.

Synthesis of Intermediate 1-3

84 g acenaphthene-quinone, 72.8 g 1,3-diphenyl acetone, 600 ml ethanol, 56 g potassium hydroxide were added into a four-necked flask under nitrogen and stirred with refluxing for 2 hours. The mixture was cooled down to the room temperature and filtered. The precipitate was rinsed with ethanol twice to get 130 g black solid, with a yield of 91%.

Synthesis of Compound 43

4.2 g Intermediate 1-2, 6.3 g intermediate 1-3 and 60 ml diphenyl ether were added into a four-neck flask under nitrogen and stirred for 10 min, then heated to reflux for 12 hours. The mixture was cooled down and filtered. The precipitate was then stirred in refluxing ethyl acetate, cooled down and filtered to get 6.5 g light yellow solid, with a yield of 66%. ¹H NMR (400 MHz, CD$_2$Cl$_2$,) δ: 7.56-7.74 (m, 9H), 7.21-7.44 (m, 14H), 7.76-7.70 (m, 1H), 1.27 (s, 6H). MALDI-TOF-MS m/z found 546.5; C$_{43}$H$_{30}$ ([M$^+$]) requires 546.2.

Embodiment 2: Synthesis of Compound 46

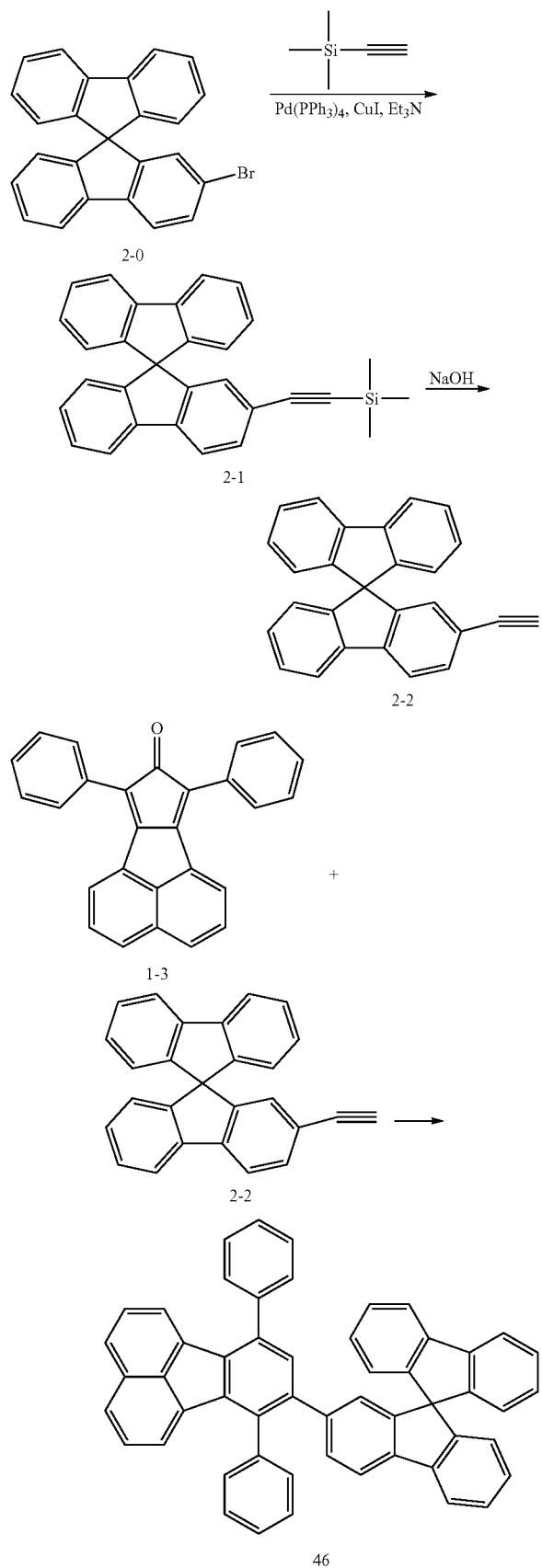

Synthesis of Intermediate 2-1

Triethylamine was added into a mixture of 8.0 g intermediate 2-0, 0.15 g cuprous iodide and 0.3 g tetrakis (triphenylphosphine)palladium under nitrogen. The starting materials were stirred until fully dissolved followed by adding 10 ml trimethylsilyl acetylene. The mixture was refluxed for 12 hours overnight, and the solvent was remove under reduced pressure. The residue was extracted three times using diethyl ether/water. The organic phase was washed three times with saturated brine, dried, filtered, and concentrated to get 6.8 g product, with a yield of 83%.

Synthesis of Intermediate 2-2

45 ml methanol, 50 ml methylene chloride, 5 g potassium hydroxide, 7 g intermediate 2-1 were added into a flask under nitrogen and stirred for 1 hour. Then the mixture was filtered to remove the inorganic salts, and the organic solvent was removed under reduced pressure. The precipitate was recrystallized from methanol to get 4.0 g product, with a yield of 70%.

Synthesis of Compound 46

Figure 2:
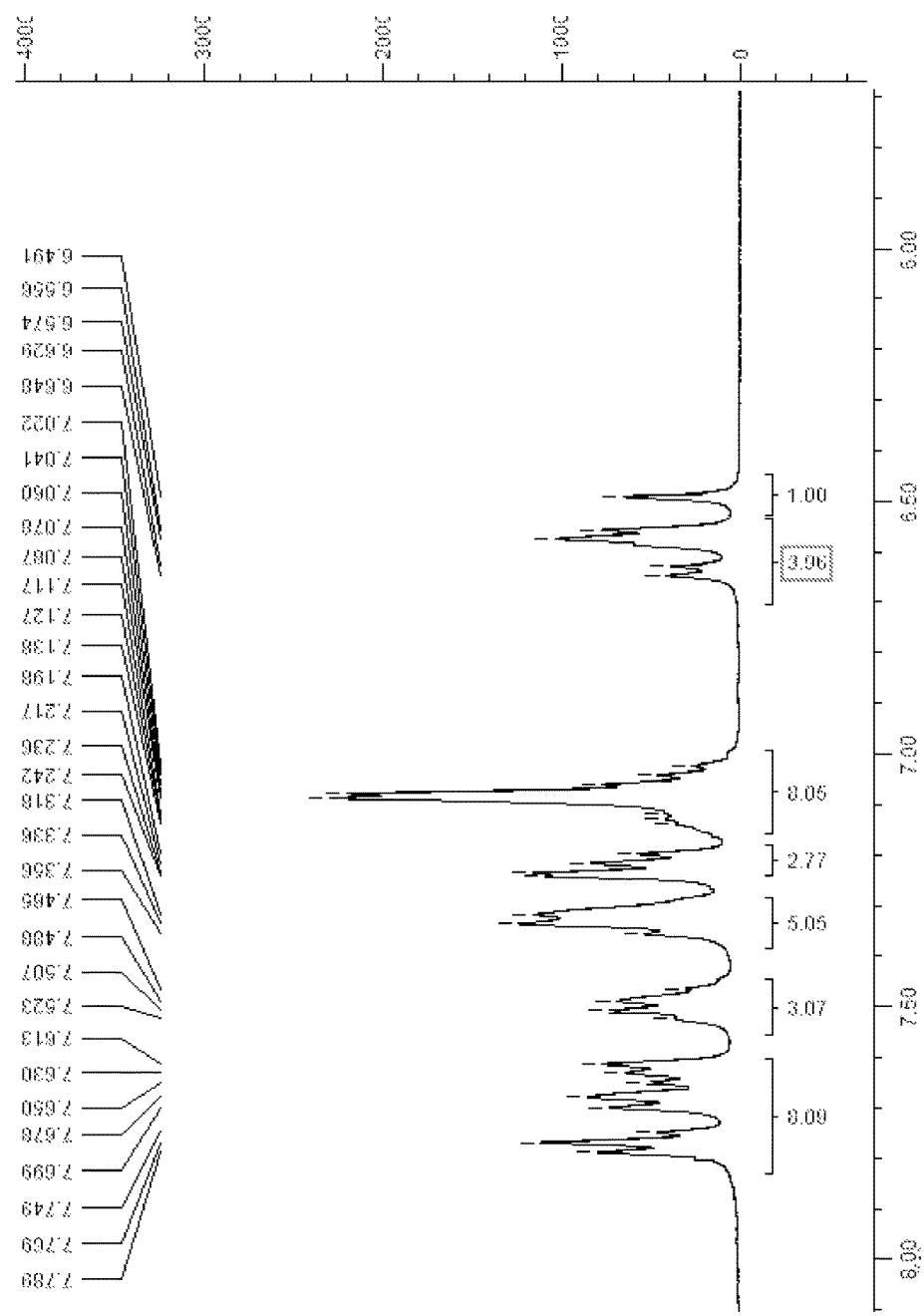
FIG. 2 is the ¹H NMR diagram of compound 46.

4.0 g Intermediate 2-2, 4.2 g intermediate 1-3 and 60 ml diphenyl ether were added into a four-neck flask under nitrogen. The mixture was stirred for 10 min before refluxing for 12 hours. The mixture was cooled down and filtered. The precipitate was washed in refluxing ethyl acetate, cooled down and filtered to get 7.0 g light yellow solid, with a yield of 89%. $^1$H NMR (400 MHz, CDCl$_3$) δ: 7.61-7.79 (m, 8H), 7.47-7.52 (m, 3H), 7.32-7.36 (m, 5H), 7.20-7.24 (m, 3H), 7.02-7.14 (m, 8H), 6.56-6.65 (m, 4H), 6.49 (s, 1H), as shown in FIG. 2. MALDI-TOF-MS m/z found 668.5, C$_{53}$H$_{32}$ ([M$^+$]) requires 668.3.

Embodiment 3: Synthesis of Compound 35

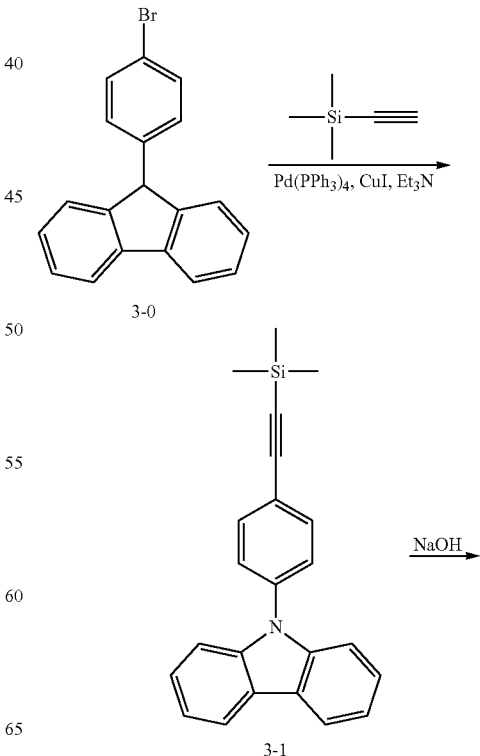

-continued

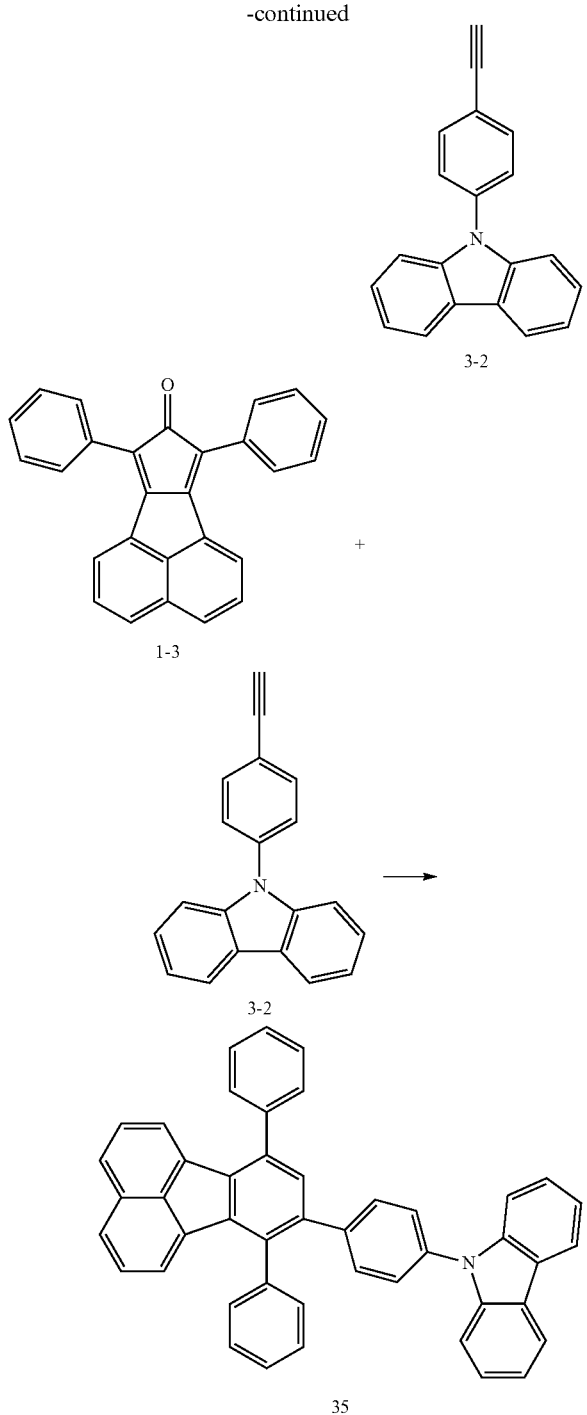

organic phase was washed three times with saturated brine, dried, filtered, and concentrated to get 6.8 g product, with a yield of 67%.

Synthesis of Intermediate 3-2

45 ml methanol, 50 ml methylene chloride, 5 g potassium hydroxide, and 5.5 g intermediate 3-1 were added into a flask under nitrogen followed by stirring for 1 hour. The mixture was filtered to remove the inorganic salts, and organic solvent was removed under reduced pressure. The precipitate was recrystallized from methanol to get 4.11 g product, with a yield of 95%.

Synthesis of Compound 35

4.0 g Intermediate 3-2, 5.5 g intermediate 1-3 and 60 ml diphenyl ether were added into a four-neck flask under nitrogen, and stirred for 10 min before heated to reflux for 12 hours. The mixture was cooled down and filtered. The precipitate was washed in refluxing ethyl acetate, then cooled down and filtered to get 4.5 g light yellow solid, with a yield of 49%. $^1$H NMR (400 MHz, $CD_2Cl_2$) δ: 8.12-8.13 (d, J=7.6 Hz, 2H), 7.74-7.77 (m, 4H), 7.52-7.60 (m, 3H), 7.25-7.45 (m, 19H), 6.69-6.81 (d, J=7.2 Hz, 1H). MALDI-TOF-MS m/z found 595.4; $C_{46}H_{29}N$ ([M$^+$]) requires 595.2.

Embodiment 4: Synthesis of Compound 26

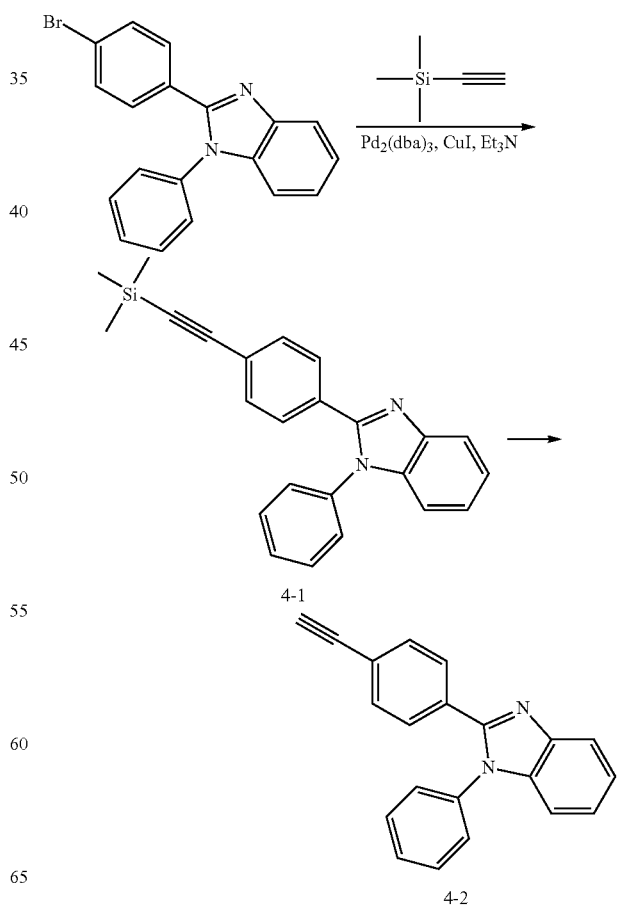

Synthesis of Intermediate 3-1

Triethylamine was added into a mixture of 7.7 g intermediate 3-0, 0.15 g cuprous iodide, and 0.3 g tetrakis(triphenylphosphine)palladium under nitrogen. The starting materials were stirred until fully dissolved, and then 10 ml trimethylsilyl acetylene was added, followed by refluxing the mixture for 12 hours overnight. The solvent was removed under reduced pressure, and the resulting residue was extracted three times using diethyl ether/water. The

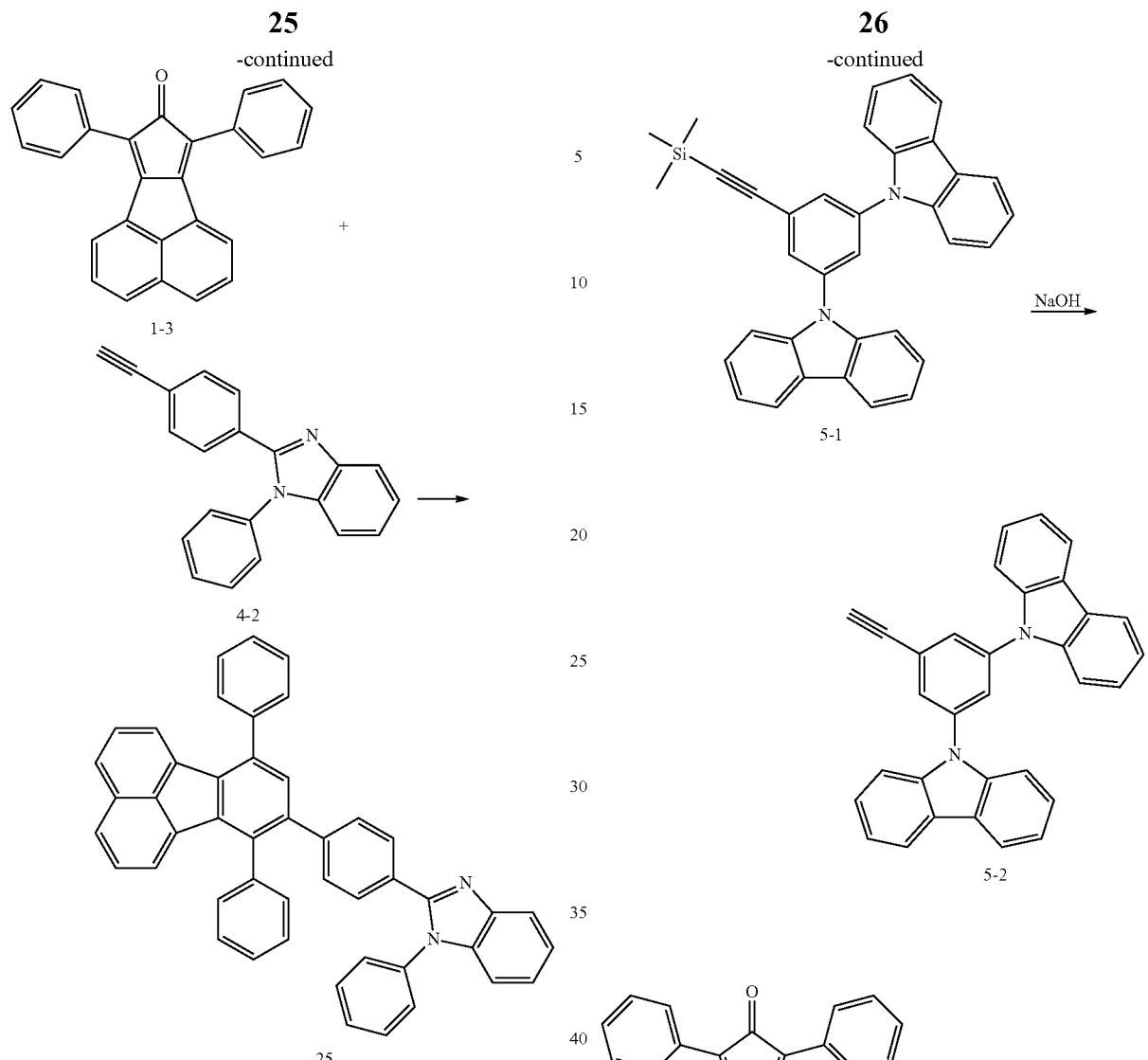
The synthesis process is the same as that of embodiment 1
Embodiment 5
Synthesis of Compound 36
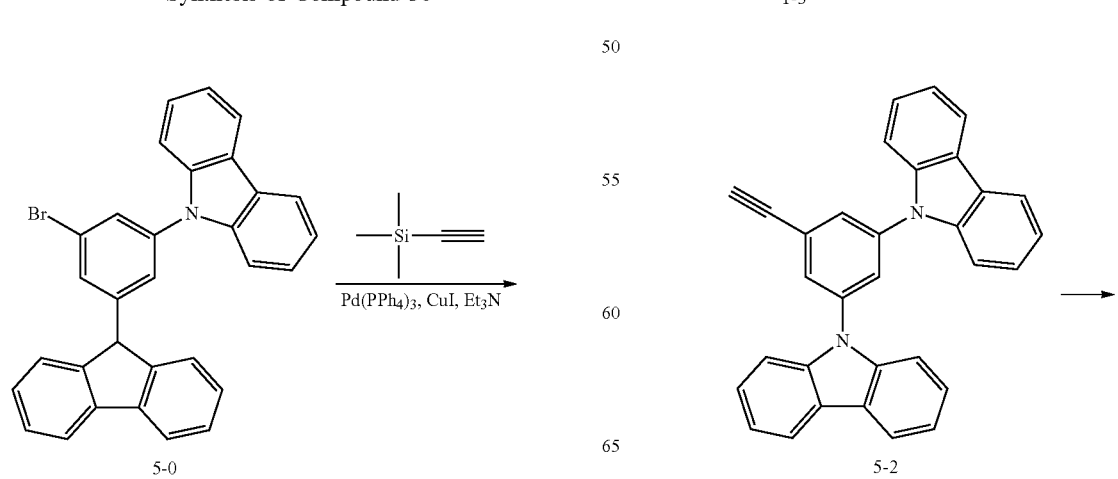

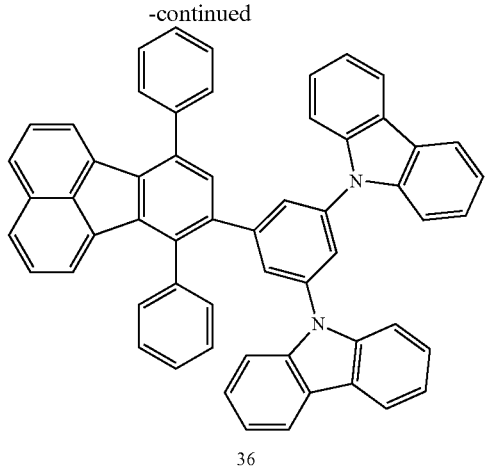

36

Synthesis of Intermediate 5-1

100 ml triethylamine was added into a mixture of 9.1 g compound 5-0, 0.15 g cuprous iodide, and 0.24 g tetrakis (triphenylphosphine)palladium under nitrogen. The starting materials were stirred until fully dissolved, and then 10 ml trimethylsilyl acetylene was added, followed by refluxing for 12 hours overnight. The solvent was removed under reduced pressure, and the resulting residue was extracted three times using diethyl ether/water. The organic phase was washed three times with saturated brine, dried, filtered, and concentrated to get 6.8 g product, with a yield of 74%.

Synthesis of Intermediate 5-2

45 ml methanol, 50 ml methylene chloride, 5 g potassium hydroxide, and 7 g intermediate 2-1 were added into a flask under nitrogen followed by stirring for 1 hour. The mixture was filtered to remove the inorganic salts, and the organic solvent was removed under reduced pressure. The precipitate was recrystallized from methanol to get 5.0 g product, with a yield of 83%.

Synthesis of Compound 36

Figure 3:
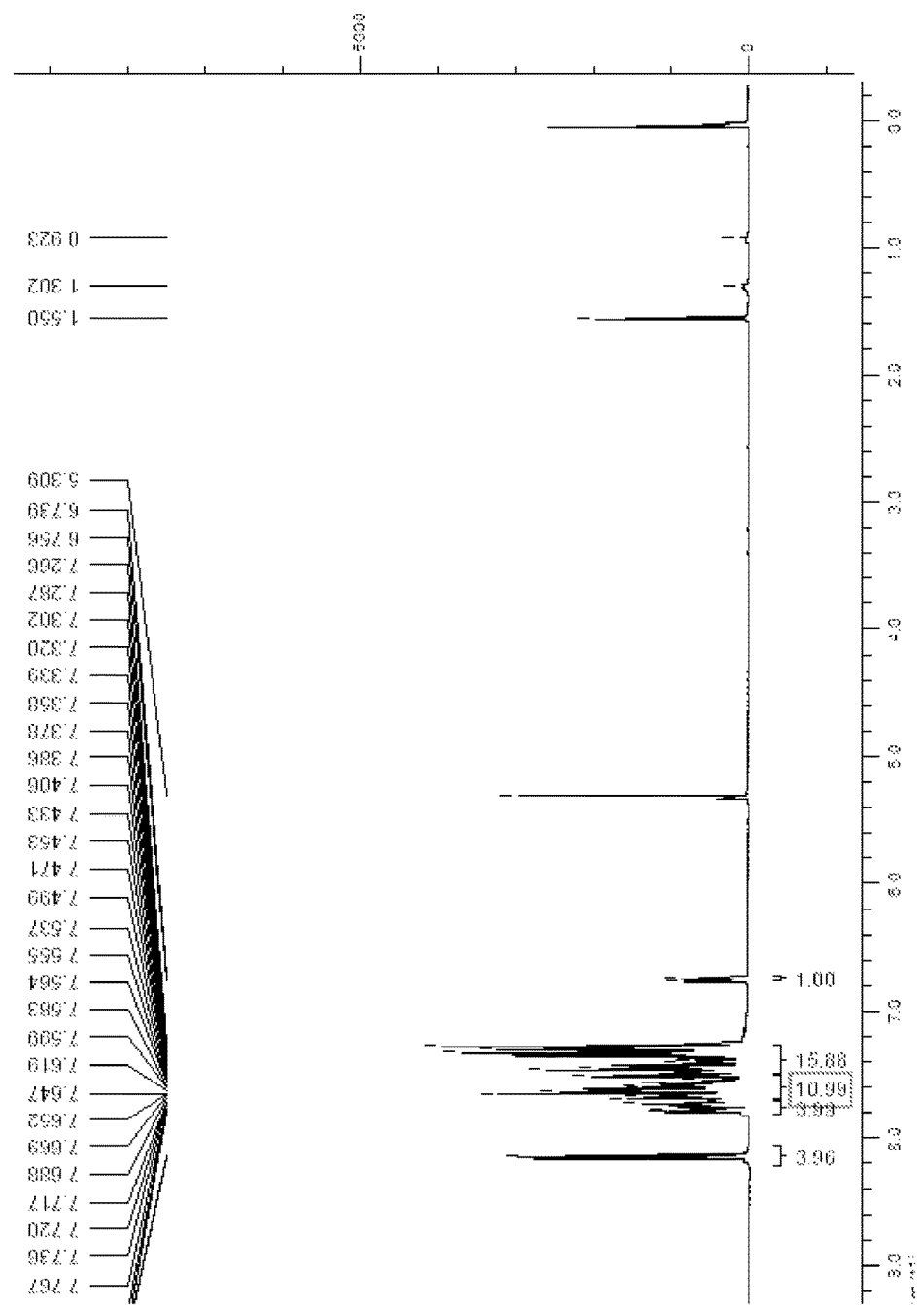
FIG. 3 is the ¹H NMR diagram of compound 36.
Figure 4:
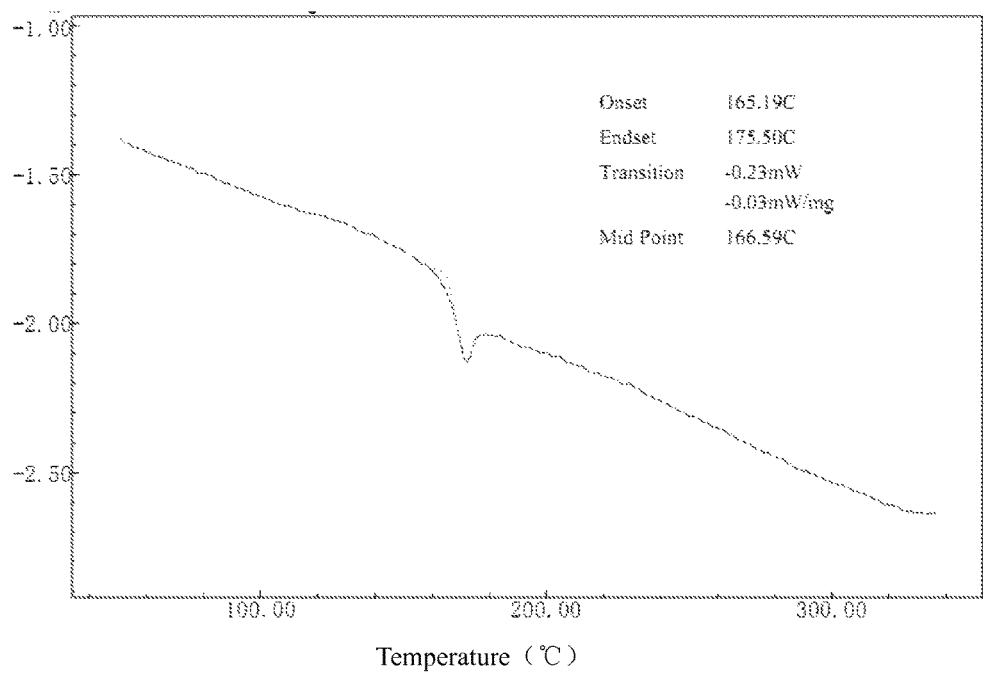
FIG. 4 is the DSC diagram of compound 46.

4.8 g intermediate 6-2, 3.9 g intermediate 1-3 and 60 ml diphenyl ether were added into a four-neck flask under nitrogen. The mixture was stirred for 10 min before heated to reflux for 12 hours. The mixture was cooled down and filtered. The precipitate was washed in refluxing ethyl acetate, cooled down and filtered to get 5.5 g light yellow solid, with a yield of 66%. $^1$H NMR (400 MHz, CD$_2$Cl$_2$) δ: 8.14-8.16 (d, J=8.4 Hz, 4H), 7.72-7.80 (m, 4H), 7.54-7.69 (m, 11H), 7.27-7.50 (m, 16H), 6.74-6.76 (d, J=6.8 Hz, 1H), as shown in FIG. 3. MALDI-TOF-MS m/z found 760.5; C$_{59}$H$_{36}$N$_2$ ([M$^+$]) requires 760.3.

Embodiment 6

With the protection of nitrogen, the glass transition temperature of the compound 26 was measured using DSC method at a heating and cooling rate of 20° C./min. The measured glass transition temperature Tg of Compound 26 is 140° C. The glass transition temperatures of compounds 35, 36, 43, 46 are measured using the same procedures. The results are listed in the following table 1.

Comparison Example 1

The glass transition temperatures of compounds mCP and BCP were measured using the same test procedures as stated in Embodiment 6. The results are also listed in the following table 1.

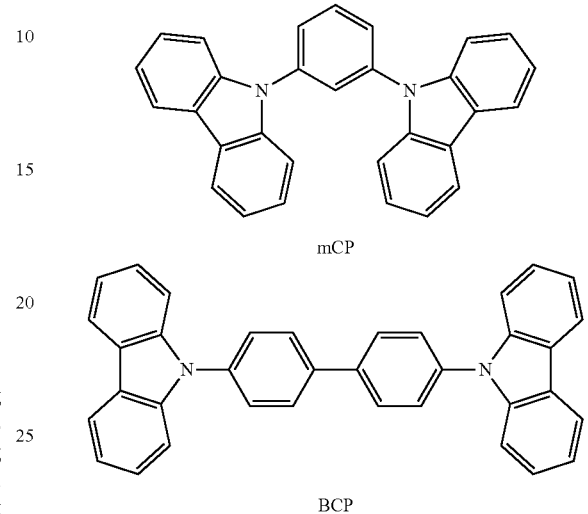

mCP

BCP

|  | Compound | Glass transition temperature (Tg)/° C. |
|---|---|---|
| Embodiment | Compound 26 | 140 |
|  | Compound 35 | 132 |
|  | Compound 36 | 169 |
|  | Compound 43 | 90 |
|  | Compound 46 | 167 |
| Comparison Example | mCP | 55 |
|  | BCP | 62 |

As shown from table 1, the compounds in the present invention have higher glass transition temperatures than some conventional host materials in the market. This invention has improved the thermal stability of the electroluminescent materials.

Embodiment 7

OLED was fabricated adopting the organic electronic material in the present invention. The structure of device is shown in FIG. 1.

Firstly, the transparent and conductive ITO substrate (with the ITO layer 20 above the glass 10) was washed with detergent solution, deionized water, ethanol, acetone, deionized water in sequence, then treated with oxygen plasma for 30 seconds, and then treated with CF$_x$ plasma.

Then on ITO was vacuum evaporated 5 nm MoO$_3$ as the hole injection layer 30.

Then 50 nm thick TAPC was vacuum evaporated as the hole transport layer 40.

Then on top of the hole transport layer was evaporated 10 nm light emitting layer, which comprises compound 35 as a host material and 10% FIrpic as a blue phosphorescent material.

Then, 50 nm thick TmPyPb was vacuum-evaporated as an electron transport layer 60 on top of the light emitting layer.

Finally, 1.2 nm LiF, 150 nm Al were evaporated as the electron injection layer 70 and the cathode, respectively.

The OLED produced as mentioned above can achieve a current density of 0.28 mA/cm² under a driving voltage of 4V with blue emission.

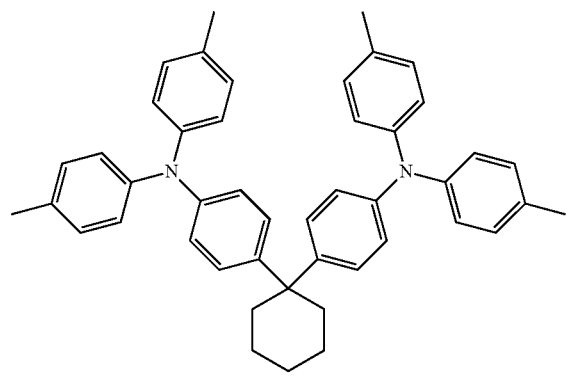

TAPC

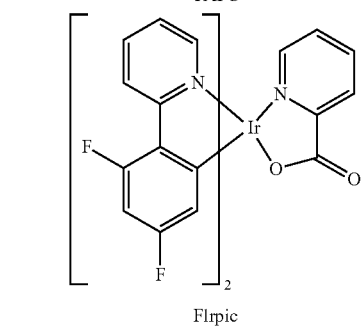

FIrpic

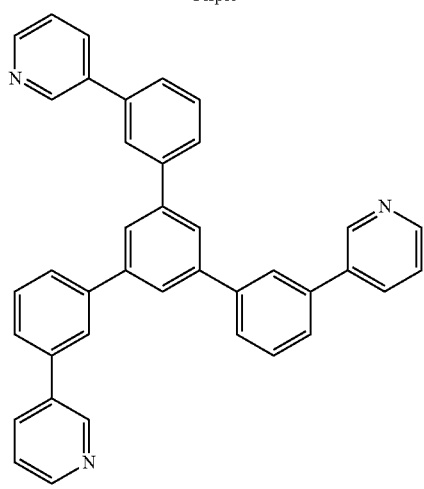

TmPyPb

Comparison Example 2

The device structure was the same as that in Embodiment 7, but the compound 35 was replaced by CBP.

The OLED produced in the comparison example can achieve a current density of 0.17 mA/cm² under a driving voltage of 4V with blue emission. Therefore, compared with conventional materials, the materials in the present invention can give higher current density at the same driving voltage, improving the light-emitting performance.

What is claimed is:

1. An organic electronic material having the structure of formula (II) as described below:

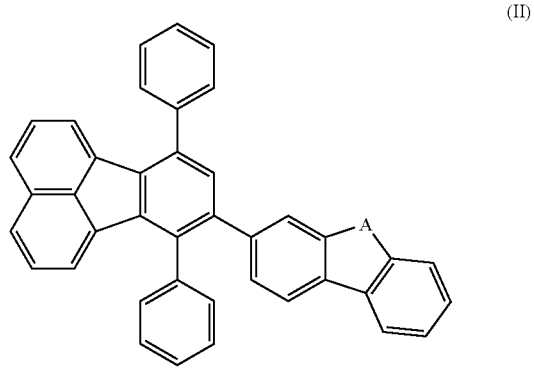

(II)

wherein,
A is selected from $C(R_6)_2$, $N(R_7)$, S, O, $P(R_8)$, $S(O)_2$ or $B(R_9)$,
when A is selected from $N(R_7)$, S, O, $P(R_8)$, $S(O)_2$, or $B(R_9)$, $R_7$-$R_9$ independently represent hydrogen, deuterium, alkyl, phenyl, alkylphenyl, heteroaromatic ring with one or more heteroatoms (N, O, S), a cyclized structure formed between two R6 and C,
when A is $C(R_6)_2$, $R_6$ represents alkylphenyl, heteroaromatic ring with one or more heteroatoms (N, O, S), a cyclized structure formed between two R6 and C.

2. An organic light-emitting material according to claim 1, wherein A is $N(R_7)$, S, O, or $S(O)_2$; and $R_7$ represents hydrogen, methyl, phenyl, or methyl phenyl, or five-membered cyclic structure formed between two R6 and C.

3. The organic electronic material according to claim 1, wherein the structure is one shown below:

-continued

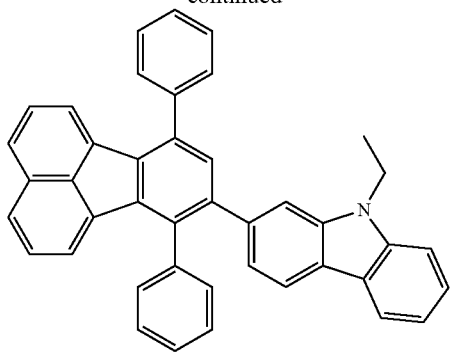

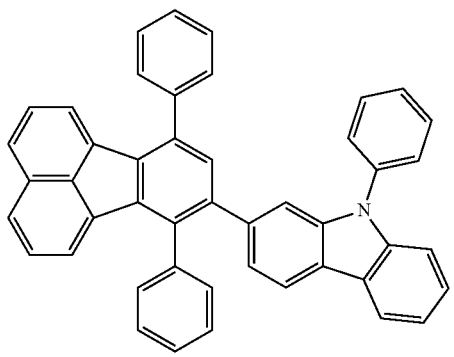

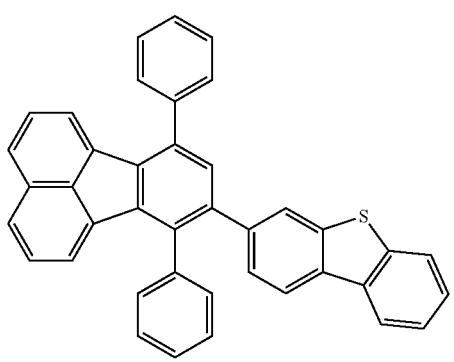

-continued

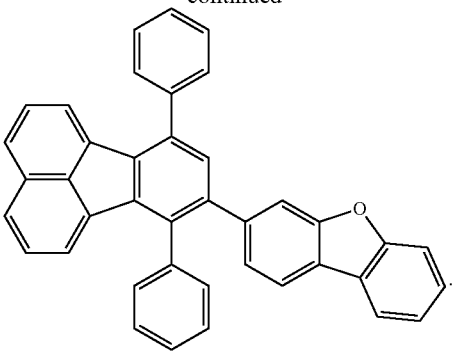

4. The organic electronic material according to claim 1, wherein the structure is one shown below:

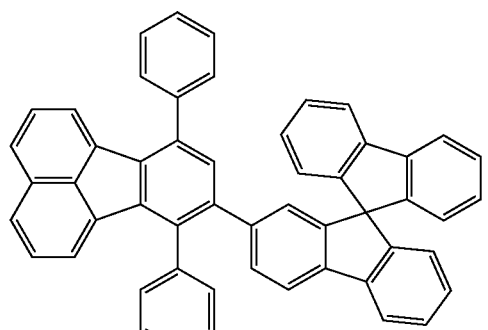

or

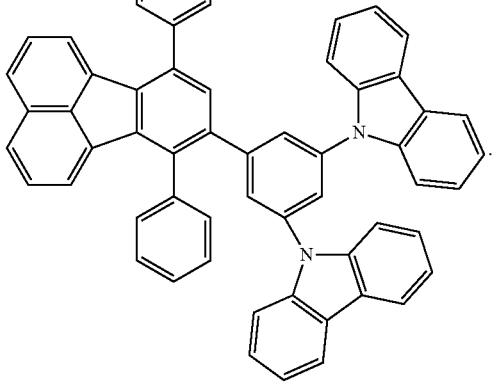

5. An OLED containing the organic electronic material as stated in claim 1.

6. The OLED according to claim 5, comprising a hole injection layer, a hole transport layer, a light emitting layer, an electron transport layer or/and an electron injection layer, wherein, the organic electronic material as stated in claim 1 is used in any one layer or multiple layers of hole injection layer, hole transport layer, light emitting layer, electron transport layer or/and electron injection layer.

7. The OLED according to claim 6, wherein the organic electronic material is used in the electron transport layer.

8. The OLED according to claim 6, wherein the said light-emitting layer comprises a host material and a guest material, and the organic electronic material is the host material for red phosphorescent dopant in the light-emitting layer.

9. The OLED according to claim 8, wherein the guest material is an organic iridium compound or an organic platinum compound.

10. The OLED according to claim 8, wherein the organic electronic material is used in the electron transport layer.

11. The OLED according to claim 9, wherein the organic electronic material is used in the electron transport layer.

12. The organic electronic material according to claim 1, when A is $C(R_6)_2$, $R_6$ represents alkylphenyl, heteroaromatic ring with one or more heteroatoms (N, O, S), a cyclized structure formed between two R6 and C.

13. The organic electronic material according to claim 1, The organic electronic material according to claim 1, wherein the structure is one shown below:

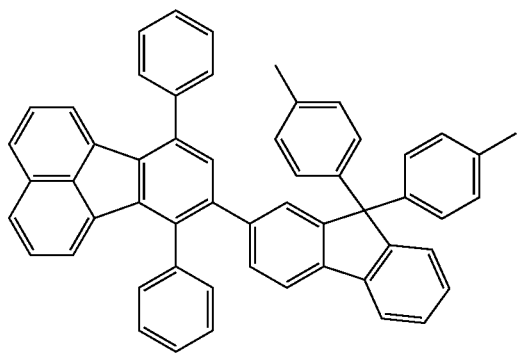

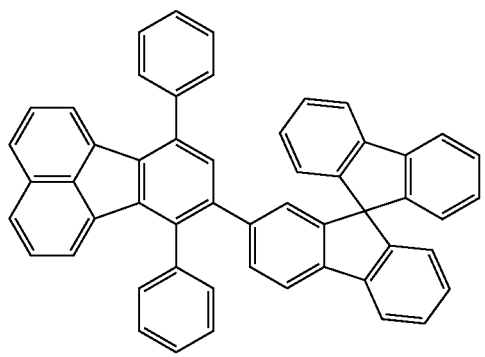

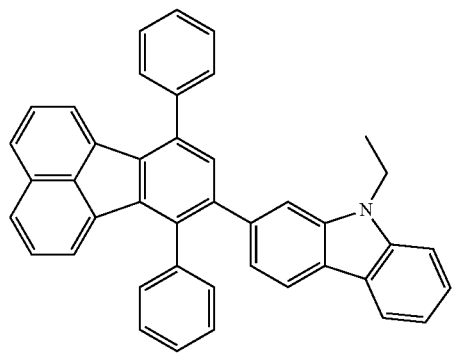

-continued

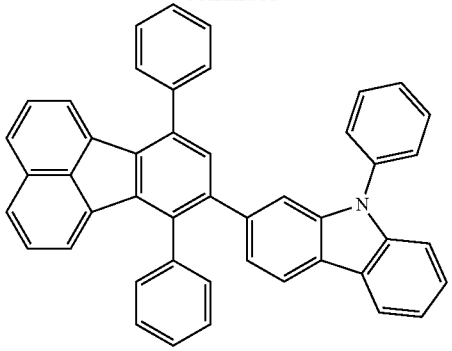

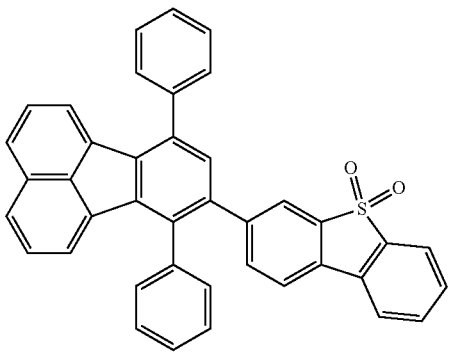

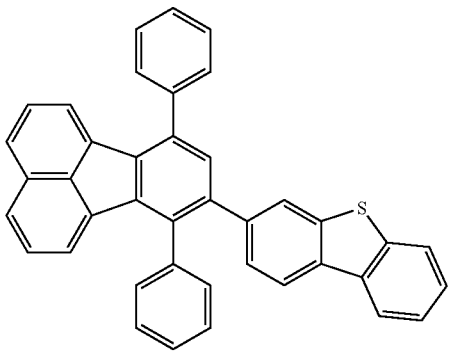

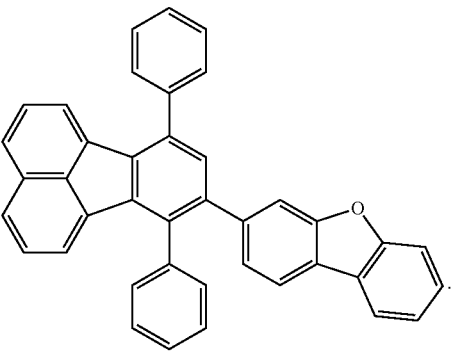 [SMILES: c1ccc(-c2cc(-c3ccc4c(c3)oc3ccccc34)c(-c3ccccc3)c3c2-c2cccc4cccc-3c24)cc1]

14. The organic electronic material according to claim 1, wherein the structure is one shown below:

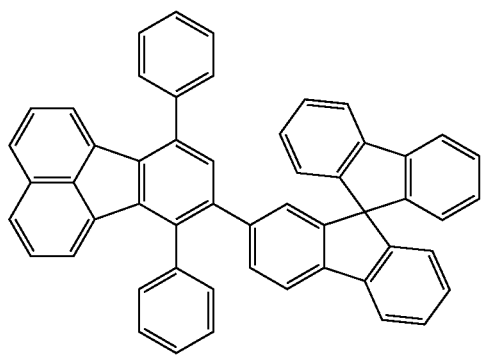
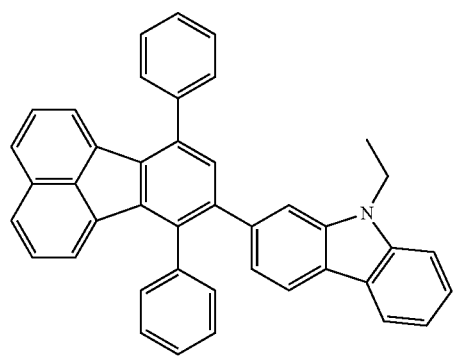
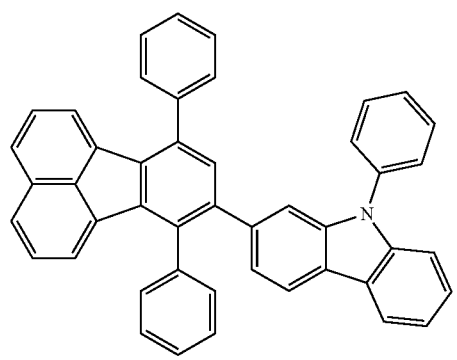
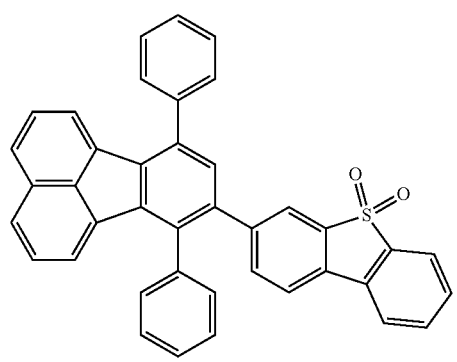
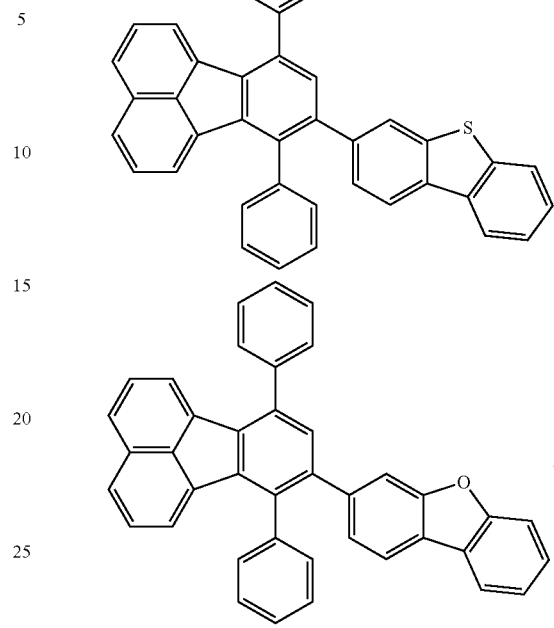
15. The organic electronic material according to claim 1, wherein the structure is shown below:
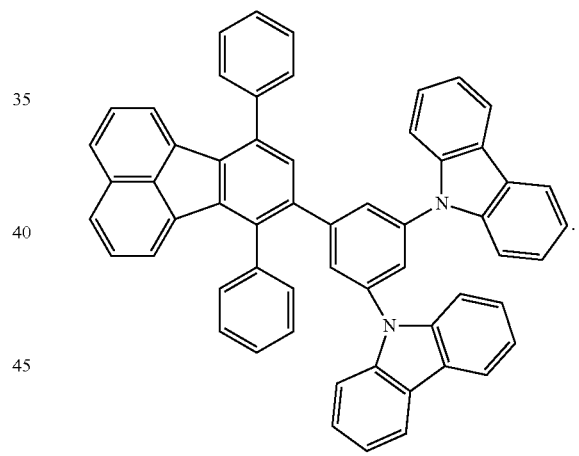
16. The organic electronic material according to claim 1, wherein the structure is one shown below:
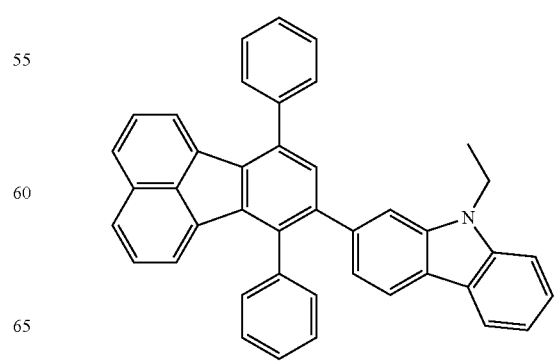

37
-continued

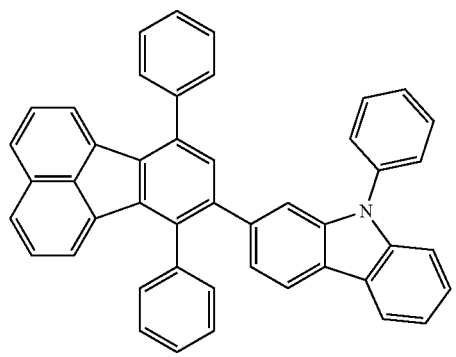

38
-continued

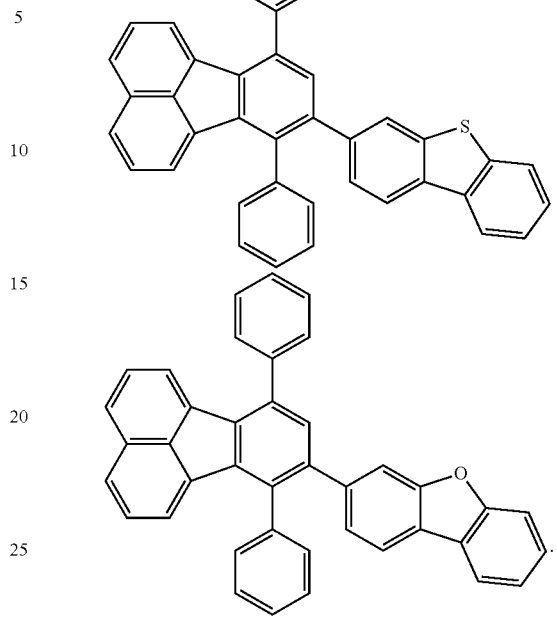

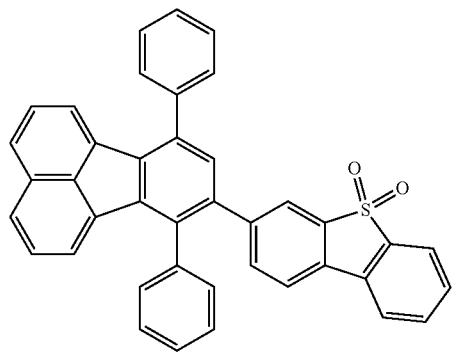

17. The organic electronic material according to claim 1, wherein,
    A is selected from $N(R_7)$, S, O, $P(R_8)$, $S(O)_2$ or $B(R_9)$, and $R_7$-$R_9$ are independently represent hydrogen, deuterium, alkyl, phenyl, alkylphenyl, heteroaromatic ring with one or more heteroatoms (N, O, S), a cyclized structure formed between two R6 and C.

18. An OLED containing the organic electronic material as stated in claim 3.

19. An OLED containing the organic electronic material as stated in claim 17.

* * * * *